United States Patent [19]

Gutman

[11] 4,331,681

[45] May 25, 1982

[54] METHOD FOR CONTROLLING ALGAE

[75] Inventor: Arnold D. Gutman, Berkeley, Calif.

[73] Assignee: Stauffer Chemical Company, Westport, Conn.

[21] Appl. No.: 221,118

[22] Filed: Dec. 29, 1980

[51] Int. Cl.³ ............................................. A01N 37/34
[52] U.S. Cl. ................................. 424/304; 260/465 K
[58] Field of Search .................... 260/465 K; 424/304

[56] References Cited

U.S. PATENT DOCUMENTS

| | | | |
|---|---|---|---|
| 3,159,532 | 12/1964 | Heininger et al. | 260/465 G X |
| 3,159,666 | 12/1964 | Heininger et al. | 260/465 G |
| 4,079,148 | 3/1978 | Oeckl et al. | 424/304 |

*Primary Examiner*—Dolph H. Torrence
*Attorney, Agent, or Firm*—Joel G. Ackerman

[57] ABSTRACT

Algae are controlled or inhibited by application of an algicidally effective amount of the compound 3-(4-tolylsulfonyl)acrylonitrile.

1 Claim, No Drawings

METHOD FOR CONTROLLING ALGAE

This invention relates to a method of controlling algae by the use of the compound 3-(4-tolylsulfonyl)acrylonitrile, which has the formula

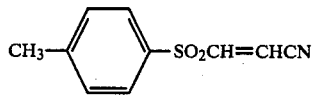

used in an algicidally effective amount, and also to compositions for control of algae containing an algicidally effective amount of this compound.

Algicidal evaluation of this compound was performed using the following procedure.

This test procedure utilizes the uptake by algae of radioactively labeled carbon dioxide ($^{14}CO_2$) generated from labeled sodium bicarbonate and an acid to simulate short term photosynthesis, and the ability of toxicants to inhibit this process. The inhibition of carbon dioxide uptake by toxic materials is a relevant parameter indicating aligicidal activity, as algae utilize $CO_2$ as their primary carbon source during normal photosynthetic metabolism.

A stock solution of the compound to be tested was prepared by dissolving the compound in water or water containing a small amount (4% by volume or less) of a solvent for the test compound, to produce a solution containing 1600 μg/ml. of the test compound. This stock solution was then diluted with water to produce test solutions of the compound containing from 800 μg/ml., downwards.

Into a Microtiter there was put 50 μl of a suspension of the test algae, 25 μl of radioactive $^{14}$carbon labeled sodium bicarbonate solution in sterile $10^{-2}$ molar dipotassium acid phosphate and 25 μl of the solution of the toxicant in an amount so as to give the desired compound concentration in a total volume of 100 μl including the toxicant, algae suspension and sodium bicarbonate solution.

The Microtiter plates were then covered with transparent tape to eliminate loss of sample volume through evaporation. Carbon dioxide uptake was allowed to proceed for four hours at ambient temperature under continuous illumination from cool white fluorescent lamps. At the end of this time, the tape was removed, the samples stirred and 50 μl removed from each by pipet. The removed material was vacuum filtered through a millipore filter, and the filters were washed with distilled water and air dried for 10–15 minutes. The filters were then placed into 10 ml. of a liquid scintillation fluid in a scintillation vial. The sample vials were then counted in a liquid scintillation counter which had settings optimized for $^{14}C$ counting. The appropriate background counts were deducted from the experimental values.

Duplicate negative controls were run in which the toxicant was replaced by 25 μl of sterile distilled water. Positive controls were also incorporated into the test using cupric sulfate pentahydrate.

The duplicate four hour controls for each species of algae were averaged. Each algicide concentration result was then determined and converted to a percent reduction of the carbon dioxide uptake using the negative controls as 100%. The concentration of the test compound which gave a 50% reduction of $CO_2$ uptake is called the $I_{50}$ value for that compound. Test compounds are considered effective against algae if the $I_{50}$ value is less than or equal to 100 μg/ml.

Four species of algae were utilized in this test: *Chlorella pyrenoidosa, Scenedesmus obliquus, Anacystis nidulans,* and *Anabaena flos-aquae*. The latter two are blue-green algae.

In this test, the compound had an $I_{50}$ as follows:
*Chlorella pyrenoidosa:* 5;
*Scenedesmus obliquus:* 1.5;
Anacystis nidulans and *Anabaena flos-aquea:* less than 1.

For use in controlling or inhibiting the growth of algae, the active compound, per se or in a formulation with inert carriers or diluents and optionally other substances, is introduced into an aqueous environment in which algae are present, or may occur. The manner in which the aqueous environment is treated will vary with the specific problems encountered. The compound may be utilized for instance, in ponds, lakes and other areas in which water, particularly industrial process water or effluents, is stored. Water flowing sites such as drainage ditches may be similarly treated. The compound may be utilized for the control of algae in industrial cooling towers and other water recirculating systems.

When so used, the compound is added to the aqueous environment in an algicidally effective amount, which usually ranges from about 0.1 to about 50 ppm, preferably from about 0.1 to about 10 ppm.

Examples of algicidal formulations in which the active compound may be employed are dispersable or soluble powders or solids, or emulsifiable concentrates. Suitable carriers or diluents for use in preparation of such formulations include solvents, such as aromatic hydrocarbons (optionally chlorinated) for instance, xylene, benzene and chlorobenzenes, paraffins such as petroleum fractions, alcohols, for instance methanol or ethanol, and amines such as ethanolamine or dimethylformamide; finely divided solid carriers, for instance, natural and synthetic meals or powders including kaolin, alumina, chalk, talc, or highly dispersed silicates, emulsifiers including nonionic and anionic emulsifiers such as polyoxyethylene fatty acid esters, polyoxyethylene fatty alcohol ethers, alkyl or aryl sulfonates, or magnesium stearate or sodium oleate; and dispersing agents such as lignin, methyl cellulose, or sulfite waste liquors. Solid pellets or large tables containing the active compound may be manufactured by mixing a dispersible or solid powder formulation of said compound with a binder.

Emulsions employing the algicidal compound disclosed herein may be prepared by dissolving the active compound in a water-immiscible solvent such as aromatic hydrocarbons, petroleum fractions, and the like, in association with a surfactant such as mentioned above, to obtain an emulsifiable concentrate which is then poured into water, preferably with vigorous agitation. Emulsions may also be prepared by dissolving the active compound in a water-miscible solvent such as Carbitol (diethylene glycol monoethyl ether) or an analog of Carbitol, acetone, a lower alkanol, Cellosolve (ethylene glycol monoethyl ether), and the like to obtain a concentrate which can then be added to water containing a surfactant such as mentioned aove, preferably with vigorous agitation.

In addition to the active compound, algicidal formulations according to this invention may also contain other active ingredients suitable for control of algae, or for other uses such as control of aquatic weeds or other organisms which may be found in the environment to be treated.

What is claimed is:

1. A method for controlling or inhibiting the growth of algae comprising applying to the algae or a locus where control is desired an algicidally effective amount of the compound 3-(4-tolylsulfonyl)acrylonitrile.

* * * * *

UNITED STATES PATENT AND TRADEMARK OFFICE
Certificate

Patent No. 4,331,681                                                            Patented May 25, 1982

Arnold D. Gutman

Application having been made by Arnold D. Gutman, the inventor named in the patent above identified, and Stauffer Chemical Co., the assignee, for the issuance of a certificate under the provisions of Title 35, Section 256, of the United States Code, deleting the name of Arnold D. Gutman and adding the name of Sophia Y. Liu as the sole inventor, and a showing and proof of facts satisfying the requirements of the said section having been submitted, it is this 4th day of Dec., 1984, certified that the name of the said Arnold D. Gutman is hereby deleted from the said patent and the said Sophia Y. Liu is hereby added to the said patent as the sole inventor.

Fred W. Sherling,
*Associate Solicitor.*